(12) United States Patent
Satou et al.

(10) Patent No.: US 9,116,134 B2
(45) Date of Patent: Aug. 25, 2015

(54) INSPECTION APPARATUS FOR TUBULAR PRODUCT AND INSPECTION METHOD THEREFOR

(75) Inventors: Kouhei Satou, Amagasaki (JP); Hirotsugu Toe, Kishiwada (JP); Takafumi Satsuki, Amagasaki (JP)

(73) Assignee: NIPPON STEEL & SUMITOMO METAL CORPORATION, Tokyo (JP)

( * ) Notice: Subject to any disclaimer, the term of this patent is extended or adjusted under 35 U.S.C. 154(b) by 531 days.

(21) Appl. No.: 13/493,133

(22) Filed: Jun. 11, 2012

(65) Prior Publication Data

US 2012/0249778 A1 Oct. 4, 2012

Related U.S. Application Data

(63) Continuation of application No. PCT/JP2010/007299, filed on Dec. 16, 2010.

(30) Foreign Application Priority Data

Dec. 17, 2009 (JP) .................................. 2009-286554

(51) Int. Cl.
*H04N 7/18* (2006.01)
*G01N 21/954* (2006.01)
*B21C 37/06* (2006.01)
*B21C 51/00* (2006.01)
*G01B 11/06* (2006.01)
*G01B 11/10* (2006.01)

(52) U.S. Cl.
CPC .............. *G01N 21/954* (2013.01); *B21C 37/06* (2013.01); *B21C 51/00* (2013.01); *G01B 11/06* (2013.01); *G01B 11/105* (2013.01)

(58) Field of Classification Search
CPC ........................ G01N 21/88; G01N 2021/8816
USPC ........................................................ 348/131
See application file for complete search history.

(56) References Cited

U.S. PATENT DOCUMENTS

2006/0126060 A1* 6/2006 Colle et al. .................. 356/239.4
2009/0040503 A1* 2/2009 Kilian et al. ..................... 356/23

FOREIGN PATENT DOCUMENTS

| JP | 51-81641 | 7/1976 |
|---|---|---|
| JP | 02-93347 | 4/1990 |
| JP | 02-194309 | 7/1990 |
| JP | 05-240619 | 9/1993 |
| JP | 05-240620 | 9/1993 |
| JP | 06-51812 | 7/1994 |
| JP | 2005-134294 | 5/2005 |
| JP | 2009-115526 | 5/2009 |

* cited by examiner

*Primary Examiner* — Richard Torrente
(74) *Attorney, Agent, or Firm* — Clark & Brody

(57) ABSTRACT

An inspection apparatus includes: a camera for acquiring an image of the whole area of an end face of the tubular product; a first light source for illuminating an outer peripheral edge of the end face side of the tubular product over the entire circumference thereof, a second light source for illuminating an inner peripheral edge of the end face side of the tubular product over the entire circumference thereof; and a third light source for illuminating an inner peripheral surface of the end face side of the tubular product over the entire circumference thereof. The apparatus uses the image of the tubular product using the first and second light sources to calculate an outer diameter and a wall thickness of the tubular product and illumination from the third light source for detecting a surface defect on the inner peripheral surface of the tubular product.

16 Claims, 5 Drawing Sheets

INSPECTION APPARATUS FOR TUBULAR PRODUCT AND INSPECTION METHOD THEREFOR

TECHNICAL FIELD

The present invention relates to an apparatus for inspecting a tubular product, particularly to an inspection apparatus that acquires an image of the whole area of an end face of the tubular product and performs image processing to measure the outer diameter and the wall thickness of the tubular product, and further to detect defects on the inner surface of the tubular product.

BACKGROUND ART

A tubular product in the present invention includes tubes in which the inner circumference or outer circumference of the cross-section thereof has a shape other than a circular shape, for example, tubes having special shapes including, as a specific example, a finned tube in which fins protruded from the inner peripheral surface or the outer peripheral surface lie along the tube axis direction, and being used as a heat transfer tube in an ethylene plant, etc.

Examples of the method for automatically measuring the outer diameter and the wall thickness of a tubular product include a method that utilizes a contact type measurement instrument, one that utilizes a laser, one that utilizes a camera, and the like.

The method that utilizes a contact type measurement instrument includes, for example, a method described in Patent Literature 1, in which the measurement apparatus tends to be huge in scale.

In the method that utilizes a laser, since a special mechanism for rotating the tubular product or the laser apparatus (including a light receiving element) to measure the whole circumference of the tubular product, the measurement apparatus will be huge in scale, similarly to the method that utilizes a contact type measurement instrument. Therefore, in these two methods described above, it is difficult to measure the wall thickness of a longer-length tubular product.

In contrast to these methods, the method that utilizes a camera is capable of dimensional inspection of a tubular product with a simple configuration, and moreover is highly promising as a technique which can be easily automated. Examples of the prior art for measuring the outer diameter and wall thickness of a tube by utilizing a camera include techniques disclosed in Patent Literatures 2 to 4 listed below.

However, the apparatuses disclosed in each Patent Literature have various problems. For example, when the dimensional measurement apparatus disclosed in Patent Literature 2 is used, halation occurs on the image acquired by the camera due to the reflection of light that is projected to the tube end face, making it difficult to distinguish the external and internal contours of the tube from the image. Further, since this apparatus projects light onto the inner peripheral surface as well as the end face of the tube, a significant difference in luminance hardly occurs between the tube end face and the inner peripheral surface on the image acquired by the camera, and thus it is difficult to distinguish the internal contour of the tube from the image.

The dimensional measurement apparatus disclosed in Patent Literature 3 also has difficulty in distinguishing the external and internal contours of the tube from the image acquired by the camera as with the dimensional measurement apparatus disclosed in Patent Literature 2. Further, the dimensional measurement apparatus disclosed in this can measure only a partial area of the tube along a circumferential direction. In order to measure the whole circumference of the tube, a special mechanism for rotating the tube or each camera (including each light source) about the central axis of the tube is necessary, and therefore the measurement apparatus will be huge in scale.

In the dimensional measurement method disclosed in Patent Literature 4, since it is necessary to dispose a camera and a light source with the tube being interposed therebetween, the measurement apparatus will be huge in scale. Therefore, it is difficult to measure a long-length tube.

Moreover, to ensure the quality of the tube, an inner surface inspection for detecting surface defects such as cracks and flaws which may be present on the inner peripheral surface of the tube is performed in addition to the dimensional inspection for measuring the outer diameter and the wall thickness of tube. Since, heretofore, the inner surface inspection of tube is performed through visual inspection by workers, there is a risk that defects may not be detected. For this reason, there is a need for automating the inner surface inspection of tube.

CITATION LIST

Patent Literature

[Patent Literature 1] Japanese Patent Application Publication No. 51-81641
[Patent Literature 2] Japanese Patent Application Publication No. 5-240619
[Patent Literature 3] Japanese Patent Application Publication No. 5-240620
[Patent Literature 4] Japanese Patent Application Publication No. 2009-115526

SUMMARY OF INVENTION

Technical Problem

It is an objective of the present invention to provide an inspection apparatus for a tubular product having the following characteristics (1) and (2), and an inspection method therefor.

(1) Capable of performing dimensional inspection for the outer diameter and the wall thickness of tube by using a camera, and (2) capable of performing the inspection for a longer-length tubular product with a compact inspection apparatus.

Further, it is another objective of the present invention to provide an inspection apparatus for a tubular product having the following characteristic (3) in addition to the characteristics (1) and (2) described above, and an inspection method therefor.

(3) Capable of performing automated inspection for surface defects on the inner peripheral surface of tube, such as cracks and flaws.

Solution to Problem

The summaries of the present invention are as follows.

(I) An apparatus for inspecting a tubular product, the apparatus including:

a camera disposed on the central axis of the tubular product, the camera acquiring an image of the whole area of an end face of the tubular product;

a first light source in which light as being inclined relative to the central axis of the tubular product is emitted from outside an image acquiring part of the camera to illuminate an outer peripheral edge of the end face side of the tubular product over the entire circumference thereof; and a second light source which is interposed between the first light source and the camera and in which light as being inclined relative to the central axis of the tubular product is emitted from outside the image acquiring part of the camera to illuminate an inner peripheral edge of the end face side of the tubular product over the entire circumference thereof, wherein the inspection apparatus acquires an image of the tubular product with the camera while illuminating the tubular product with the first and second light sources, and calculates an outer diameter and a wall thickness of the tubular product based on the acquired image.

The inspection apparatus of above-described (I) is preferably configured such that the first and second light sources are movable along the central axis direction of the tubular product.

The inspection apparatus of above-described (I) is preferably configured such that the first and second light sources are configured with a large number of LEDs (light emitting diodes) being arranged in the form of a ring.

The inspection apparatus of above-described (I) is preferably configured to include a support member for supporting the first light source, the second light source, and the camera, the support member having a transparent plate that abuts the end face of the tubular product.

These inspection apparatuses may also be configured to include a third light source interposed between the second light source and the camera, in which light, as being inclined relative to the central axis of the tubular product is emitted from outside the image acquiring part of the camera to illuminate an inner peripheral surface of the end face side of the tubular product over the entire circumference thereof, wherein the inspection apparatus acquires an image of the tubular product with the camera while illuminating the tubular product with the third light source, and detects surface defects on the inner peripheral surface of the tubular product based on the acquired image.

(II) A method for inspecting a tubular product, the method including the steps of:

(step 1) acquiring an image of the whole area of the end face of the tubular product with a camera while illuminating an outer peripheral edge and an inner peripheral edge of the end face side of the tubular product, respectively, over the entire circumference thereof with an individual independent light source.

(step 2) calculating an outer diameter and a wall thickness of the tubular product based on the acquired image.

The inspection method of above-described (II) may be configured to further include the steps of:

(step 3) acquiring an image of the whole area of the end face of the tubular product with the camera while illuminating an inner peripheral surface of the end face side of the tubular product over the entire circumference thereof with a light source different from the above-described light source, and (step 4) detecting surface defects on an inner peripheral surface of the tubular product based on the acquired image.

Advantageous Effects of Invention

The inspection apparatus for a tubular product and the inspection method therefor of the present invention have following remarkable advantageous effects (1) and (2).

(1) Capable of accurately performing a dimensional inspection for the outer diameter and wall thickness of tube using a camera, (2) capable of performing the inspection for a longer-length tubular product with a compact inspection apparatus.

Further, the inspection apparatus for a tubular product and the inspection method therefor of the present invention have the following remarkable advantageous effect (3) in addition to the above-described advantageous effects (1) and (2).

(3) Capable of performing an automated inspection for surface defects on the inner peripheral surface of the tube, such as cracks and flaws.

BRIEF DESCRIPTION OF DRAWINGS

FIG. 2 is a cross-sectional view to illustrate an inspection method using the inspection apparatus of the present invention, in which

FIG. 3 is a schematic view of an image acquired by the present invention, in which

FIG. 5 is a diagram showing a real image acquired by the camera at the time of dimensional inspection of an internally finned tube, in which

FIG. 6 is a diagram showing an example of a net made of steel wire which constitutes a support member for supporting the camera and the light sources, and is provided in abutting relation relative to the tubular product, in which

DESCRIPTION OF EMBODIMENTS

The present inventors have found that in order to accurately measure the dimensions of a tubular product while downsizing the inspection apparatus using a camera, it is effective to illuminate each of the outer peripheral edge and the inner peripheral edge of the tube over the entire circumference thereof by an independent light source when acquiring an image of an end face of the tube by the camera. Further, they have found that in order to perform an automated inspection on the inner surface of a tubular product, it is effective to perform image acquisition by using the same camera as used in the dimensional inspection while illuminating the inner peripheral surface of the end face side of the tube by an independent light source.

The present invention has been completed based on these findings. Hereafter, preferred embodiments of an inspection apparatus for a tubular product and an inspection method therefor of the present invention will be described.

1. Inspection Apparatus

Figure 1:
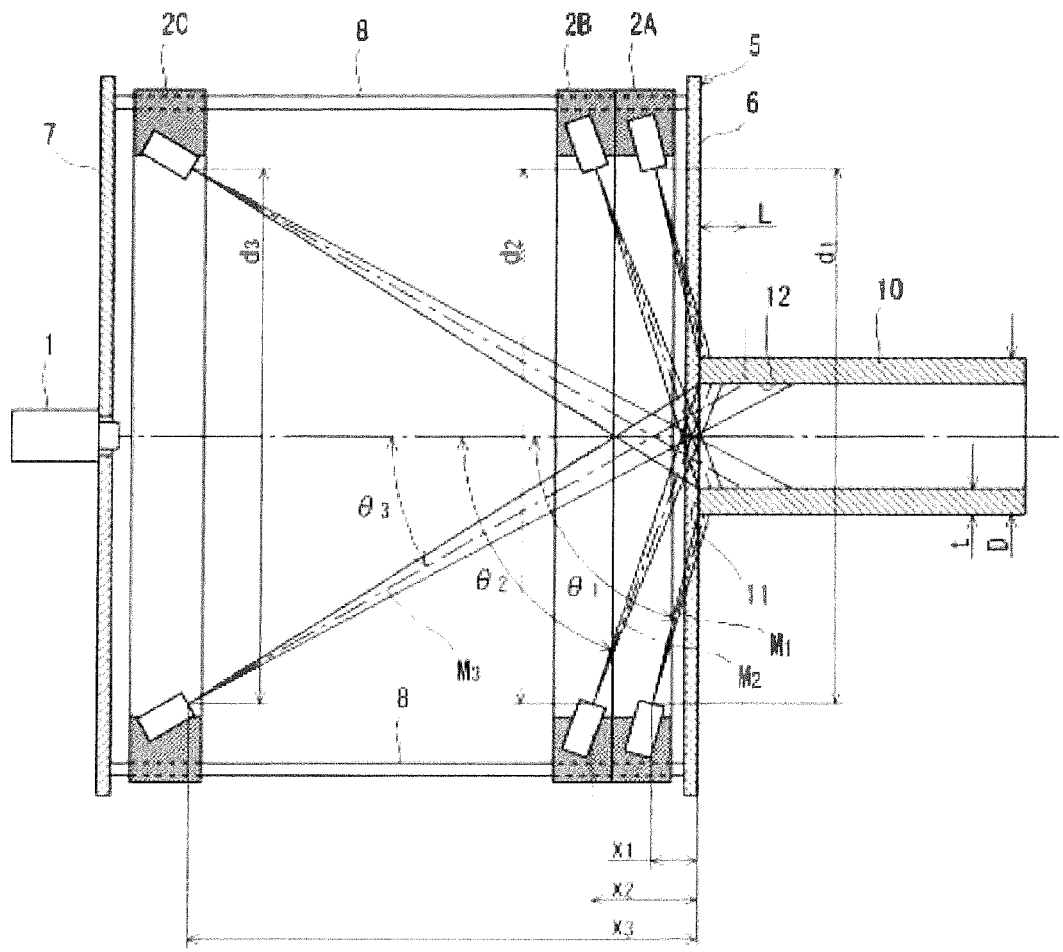
FIG. 1 is a cross-sectional view schematically showing the configuration of an inspection apparatus of the present invention.

FIG. 1 is a cross-sectional view schematically showing the configuration of an inspection apparatus of the present invention. As shown in the figure, the inspection apparatus of the present invention is applied to a dimensional inspection which, with a tubular product 10 being the object to be inspected, measures an outer diameter D and a wall thickness t of a tubular product 10, and is further applied to an inner surface inspection which detects surface defects on the inner peripheral surface 12 of the tubular product 10. Examples of the tubular product 10 to be inspected include not only steel tubes having a simple shape in which the shapes of the inner circumference and the outer circumference are circular in the cross-section, but also tubular products in which the shapes of the inner circumference and the outer circumference in the cross-section are not circular in a strict sense and are provided with regular alterations, for example, tubes having special shapes, such as an internally finned tube, an externally finned tube, and the like. FIG. 1 shows a case where the tubular product 10 is a normal tube having a concentric cross-section. The inspection apparatus includes one camera 1 for image acquisition and a light source for illumination. As for the light source, using multiple illuminations is effective, and further using an annular light source enables to realize the reduction of the number of parts and the further downsizing of the apparatus. Here is shown a case where a first annular light source 2A, a second annular light source 2B, and a third annular light source 2C are used, as light sources.

The camera 1 is disposed at a predetermined distance away from the end face 11 of the tubular product 10 such that the optical center axis coincides with the central axis of the tubular product 10, and the whole area of the end face 11 of the tubular product 10 will be the image acquiring area. The camera 1 is used at the time of dimensional inspection and also at the time of inner surface inspection. The camera 1 adopted herein is a CCD camera, and has a sufficient number of pixels such that the resolution thereof when having acquired an image of the end face 11 of the tubular product 10 at a predetermined distance apart can ensure equal to or higher accuracy than that of a measurement instrument such as a micrometer, etc.

The first annular light source 2A, the second annular light source 2B, and the third annular light source 2C are disposed in the order named between the tubular product 10 and the camera 1 such that the central axis of each of them coincides with the central axis of the tubular product 10, that is, the optical axis of the camera 1, and each of them emits an annular light which is inclined toward the end face of the tubular product 10 with respect to the central axis thereof, from outside the image acquiring part of the camera 1. Among those, any of the first annular light source 2A which is disposed closest to the tubular product 10, and the second annular light source 2B which is disposed next thereto gives adequate illumination for dimensional inspection, and the third annular light source 2C which is disposed furthest from the tubular product 10 gives due illumination for inner surface inspection.

The first annular light source 2A exclusively illuminates only the outer peripheral edge of the end face 11 side of the tubular product 10 over its entire circumference with the light which is emitted such that its optical axis $M_1$ has an inclination angle $\theta_1$ with respect to the central axis of the tubular product 10. The second annular light source 2B exclusively illuminates only the inner peripheral edge of the end face 11 side of the tubular product 10 over its entire circumference with the light which is emitted such that its optical axis $M_2$ has an inclination angle $\theta_2$ with respect to the central axis of the tubular product 10. The third annular light source 2C exclusively illuminates only the inner peripheral surface 12 of the end face 11 side of the tubular product 10 over its entire circumference with the light which is emitted such that its optical axis $M_3$ has an inclination angle $\theta_3$ with respect to the central axis of the tubular product 10.

Since each of the annular light sources 2A, 2B, and 2C is disposed such that the central axis of each annulus coincides with the central axis of the tubular product 10, it is possible to illuminate a specified area uniformly over the entire circumference.

The inclination angle $\theta_1$ of the optical axis $M_1$ of the first annular light source 2A, and the inclination angle $\theta_2$ of the optical axis $M_2$ of the second annular light source 2B are set considering that only a limited area (the outer peripheral edge and the inner peripheral edge of the end face 11 side of the tubular product 10) is illuminated, and the light reflected at the end face 11 will not enter the camera 1, at the time of dimensional inspection. For this purpose, they are preferably set, for example, within a range of not less than 60° and less than 90°. More preferably, they are within a range of 70° to 80°. Setting them in such a range allows the camera 1 to acquire an image in which the external contour and the internal contour of the tubular product 10 are marked up.

The width of illumination in a tube axis direction for the outer peripheral edge of the tubular product 10, which is illuminated by the first annular light source 2A, is permitted to be within a range of 5 mm to 10 mm from the tube end. The width of illumination in a tube axis direction for the inner peripheral edge of the tubular product 10, which is illuminated by the second annular light source 2B, is also permitted to be within a range of 5 mm to 10 mm from the tube end. That is, the lights emitted from the first annular light source 2A and the second annular light source 2B are not strictly limited to a straight parallel light beam, and may be a light beam which slightly diverges from the own center of the optical axis. However, neither of the lights illuminate the end face 11 of the tubular product 10 and, as described above, exclusively illuminate only the outer peripheral edge or the inner peripheral edge of the tube end 11 side of the tubular product 10.

The inclination angle $\theta_3$ of the optical axis $M_3$ of the third annular light source 2C is set in consideration of extending the axial length of the area as being the inner peripheral surface 12 of the tubular product 10 to be illuminated and subjected to image acquisition and inspection by the camera 1 so as to range from the end face 11 to deep inside thereof and also in consideration of avoiding the light reflected at the end face 11 to enter the camera 1, at the time of inner surface inspection. For this purpose, it is preferably set, for example, within a range of 10° to 30°.

The light emitted from the third annular light source 2C is configured to be a light beam which diverges to some extent from the own optical center. This light, however, also exclusively illuminates the inner peripheral surface 12 including the inner peripheral edge of the end face 11 side of the tubular product 10 as described above without illuminating the end face 11 of the tubular product 10.

As the first annular light source 2A, the second annular light source 2B, and the third annular light source 2C, for example, a large number of LEDs may be used which are evenly spaced in a circumferential direction and are buried in a substrate material which is made of synthetic resin etc. and formed into an annular shape. A group of LEDs arranged in a circumferential direction may be buried in a double- or triple-ring structure. In place of the LEDs, a laser apparatus may also be used which emits a visible light beam that has a small range of divergence of light beam from the center of optical axis.

The camera 1, the first annular light source 2A, the second annular light source 2B, and the third annular light source 2C described above are integrally supported by a support member 5. The support member 5 is configured to include, for example, at its fore end, a disk-shaped transparent plate 6 which is opposite to and abuts the end face 11 of the tubular product 10 at the time of inspection, and at its rear end, an annular plate 7 that holds the camera 1, in which the transparent plate 6 and the annular plate 7 are connected by multiple guide rods 8 in parallel with the central axis of the tubular product 10. Each of the annular light sources 2A, 2B, and 2C is configured to be movable along a central axis direction of the tubular product 10 along the guide rods 8, and are secured to the guide rods 8 with a screw etc. at an appropriate position.

In this way, by integrally supporting the camera 1 and each of the annular light sources 2A, 2B, and 2C by using the support member 5, the orientation and position of each of them is securely determined, and it is made possible to perform a highly accurate inspection.

An appropriate position of each of the annular light sources 2A, 2B, and 2C is set according to the dimensions of the tubular product 10 to be inspected. For example, when a tubular product 10 of an outer diameter $D_o$ and an inner diameter $D_i$ is inspected, a distance $x_1$ from the fore end face of the transparent plate 6, which abut the end face 11 of the tubular product 10, to a light emitting port in the first annular light source 2A is regarded as the position of the first annular light source 2A. To obtain this distance $x_1$, first, a calculation value $Calx_1$ is determined in the following formula (1).

$$Calx_1 = (d_1/2 - D_o/2)/\tan \theta_1 \quad (1)$$

Where, $d_1$ in the formula is a diameter of the position at which the light emitting port is arranged in the first annular light source 2A, and $\theta_1$ is an inclination angle of the optical axis $M_1$ of the first annular light source 2A. The distance $x_1$ is determined by finely adjusting the position of the calculation value $Calx_1$ such that the light of the first annular light source 2A illuminates the outer peripheral edge without illuminating the end face 11.

As the position of the second annular light source 2B, a distance $x_2$ from the fore end face of the transparent plate 6 to the light emitting port in the second annular light source 2B is set. To obtain this distance $x_2$, first, a calculation value $Calx_2$ is determined in the following Formula (2).

$$Calx_2 = (d_2/2 + D_i/2)/\tan \theta_2 \quad (2)$$

Where, $d_2$ in the formula is a diameter at which the light emitting port is arranged in the second annular light source 2B, and $\theta_2$ is an inclination angle of the optical axis $M_2$ of the second annular light source 2B. The distance $x_2$ is determined by finely adjusting the position of the calculation value $Calx_2$ such that the light of the second annular light source 2B illuminates the inner peripheral edge without illuminating the end face 11.

As the position of the third annular light source 2C, a distance $x_3$ from the fore end face of the transparent plate 6 to the light emitting port in the third annular light source 2C is set. To obtain this distance $x_3$, first, a calculation value $Calx_3$ is determined in the following Formula (3).

$$Calx_3 = (d_3/2 + D_i/2)/\tan \theta_3 - L \quad (3)$$

Where, $d_3$ in the formula is a diameter at which the light emitting port is arranged in the third annular light source 2C; $\theta_3$ is an inclination angle of the optical axis $M_3$ of the third annular light source 2C; and L is the distance of the intersection between the optical axis of the annular light source 2C and the tube inner surface, from the tube end. L can be determined to be ½ of the length of the area, over which the inspector wants to illuminate with the light from the third annular light source 2C at the time of inner surface inspection, from the tube end of the tubular product 10. The distance $x_3$ is determined by finely adjusting the position of the calculation value $Calx_3$ such that the light of the third annular light source 2C illuminates the tube inner surface so as to include the inner peripheral edge of the end face 11 side.

Each of the annular light sources 2A, 2B, and 2C respectively has a function of adjusting the quantity of light individually. This is for the purpose of making the illuminance of each of the annular light sources 2A, 2B, and 2C uniform, which is achieved by setting the quantity of light of the third annular light source 2C as being farthest away from the tubular product 10 to be illuminated to be relatively higher, while by setting the quantity of light of the first annular light source 2A as being located in the nearest distance from the tubular product 10 to be relatively lower than that of the second annular light source 2B, since the illuminance attenuates according to the distance from the light emitting port to an object to be illuminated.

2. Inspection Method

Figure 2A:
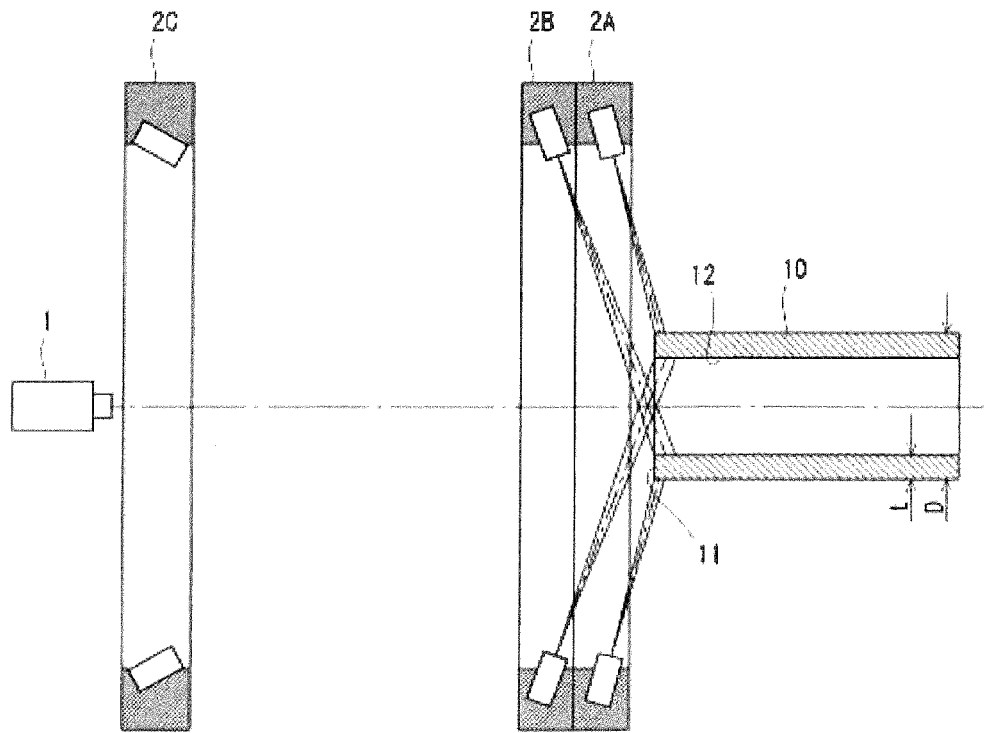
FIG. 2A shows an illumination condition at the time of dimensional inspection.
Figure 2B:
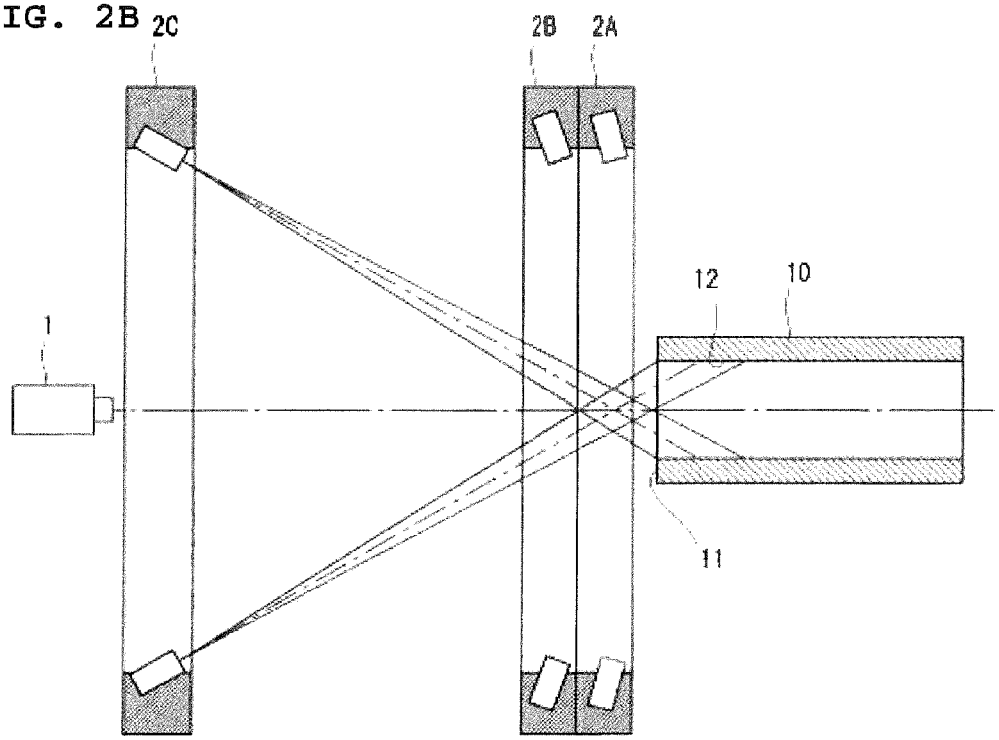
FIG. 2B shows an illumination condition at the time of inner surface inspection, respectively.
Figure 3A:
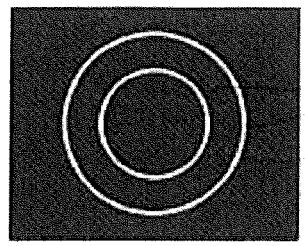
FIG. 3A shows an image for the dimensional inspection.
Figure 3B:
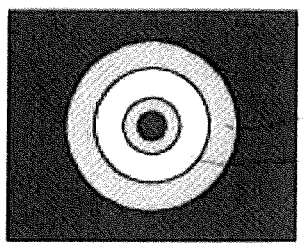
FIG. 3B shows an image for the inner surface inspection, respectively.

FIG. 2 is a cross-sectional view to illustrate an inspection method using the inspection apparatus of the present invention, in which FIG. 2A shows an illumination condition at the time of dimensional inspection, and FIG. 2B shows an illumination condition at the time of inner surface inspection, respectively. FIG. 3 is a schematic view of an image acquired by the present invention, in which FIG. 3A shows an image in a dimensional inspection, and FIG. 3B shows an image in an inner surface inspection, respectively. Incidentally, the support member 5 shown in FIG. 1 as above is not shown in FIG. 2. FIGS. 2 and 3 show a case where the tubular product 10 is a normal tube of cross section composed of concentric circles.

As shown in FIG. 2A, upon dimensional inspection of the tubular product 10, the transparent plate 6 which is the support member 5 shown in FIG. 1 described above is maintained in abutting relation relative to the end face 11 of the tubular product 10 to be inspected, and thereafter the first annular light source 2A and the second annular light source 2B are lit up so that the outer peripheral edge and the inner peripheral edge of the end face 11 side of the tubular product 10 are individually illuminated without the end face 11 thereof being illuminated. In this illumination condition, an image of the whole area of the end face 11 of the tubular product 10 is acquired by the camera 1.

Since the image by this image acquisition is obtained when only the outer peripheral edge and the inner peripheral edge of the end face 11 side of the tubular product 10 are illuminated, applying image processing such as binarization thereto will result in that, as shown in FIG. 3A, the luminance becomes very low at pixels corresponding to the end face 11 of the tubular product, and the outside and inside territories thereof that are not illuminated, and the luminance becomes high at pixels corresponding to each of the external contour 13 and the internal contour 14 of the tubular product, which are boundaries of the aforementioned areas, by being clearly marked up by the illumination. This makes it possible to determine the external contour 13 and the internal contour 14 of the tubular product based on the obtained image, and calculate the outer diameter D and the thickness t of the tubular product from the position information of those pixels. Since the calculated outer diameter D and the wall thickness t of the tubular product are based on the external contour 13 and the internal contour 14 which are clearly exhibited over the entire circumference on an image, they are highly accurate, capable of ensuring a maximum and minimum values, and excellent in reliability.

Next, as shown in FIG. 2B, when performing an inner surface inspection of the tubular product 10, the third annular light source 2C is lit up in place of the first annular light source 2A and the second annular light source 2B so that only the inner peripheral surface 12 of the end face 11 side is illuminated without the end face 11 of the tubular product 10 being illuminated. In this illumination condition, an image of the whole area of the end face 11 of the tubular product 10 is acquired by the camera 1.

Since the image by this image acquisition is obtained when only the inner peripheral surface 12 of the end face 11 side of the tubular product 10 is illuminated, applying image processing such as binarization thereto will result in that, as shown in FIG. 3B, the luminance becomes high at pixels corresponding to the inner peripheral surface 12 of the end face 11 side of the tubular product that is illuminated; the luminance becomes low at pixels corresponding to each of the end face 11 of the tubular product that is not illuminated and the inner peripheral surface 12 of deeper side of the tubular product, and the luminance becomes further lower at pixels corresponding to each of the territory outside the end face 11 and the further deep inner peripheral surface 12 of the tubular product. When surface defects are present on the inner peripheral surface 12, the luminance of pixels corresponding to the portion with the surface defect becomes higher or lower than that of the inner surface in the surrounding. This makes it possible to obtain an image which has a sufficient difference in luminance, thereby determining and detecting a surface defect from the luminance information of the pixels.

Afore-mentioned image processing, calculation of the outer diameter and wall thickness of tubular product, and determination of a surface defect on the inner peripheral surface of tubular product are executed by a computer connected to the camera 1.

Figure 4:
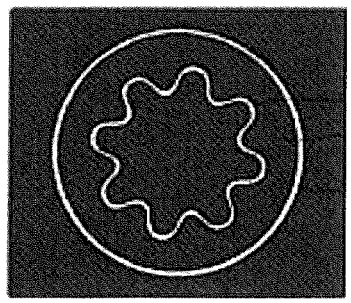
FIG. 4 is a schematic view of an image obtained when a dimensional inspection of an internally finned tube is performed by adopting the inspection method of the present invention.

FIG. 4 is a schematic view of an image obtained when a dimensional inspection of an internally finned tube is performed by adopting the inspection method of the present invention. Even when a dimensional inspection is performed with an internally finned tube as the object to be inspected, by acquiring an image of the whole area of the end face of an internally finned tube by the camera 1 with the first annular light source 2A and the second annular light source 2B shown in FIGS. 1 and 2 described above being lit up and applying image processing thereto will result in that, as shown in FIG. 4, the luminance becomes very low at pixels corresponding to each of the end face 11 of the internally finned tube and the outside and inside territories thereof, and the luminance becomes high at pixels corresponding to each of an external contour 13 of the internally finned tube, which are boundaries thereof, and an internal contour 14 including the fin portion. This makes it possible to determine the external contour 13 and the internal contour 14 of the internally finned tube based on the obtained image, and to calculate the outer diameter and the wall thickness of the internally finned tube and the height of the fin portion from the position information of those pixels.

Figure 5A:
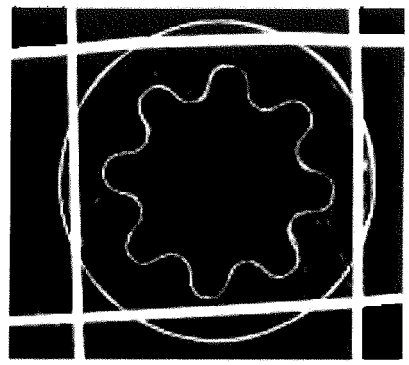
FIGS. 5A to 5C show examples when the position of the light source is moved from an arbitrary position in the range of ±10 mm along the central axis direction of the tube to be inspected.
Figure 5B:
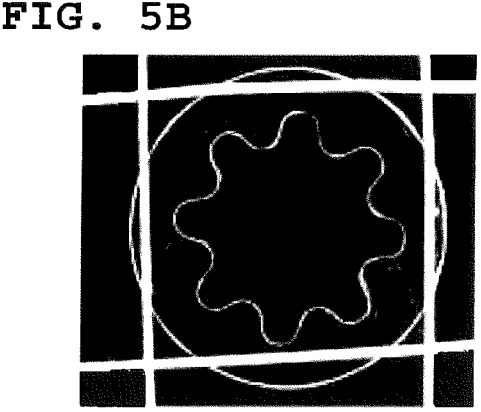
Figure 5C:
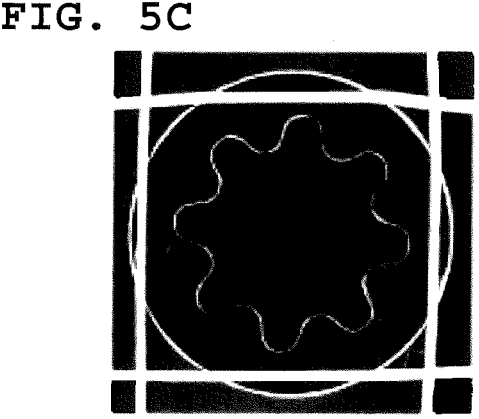

FIG. 5 is a diagram showing a real image acquired by a camera at the time of dimensional inspection of an internally finned tube, in which FIGS. 5A to 5C show one example when the position of the light source is moved from an arbitrary position along the central axis direction of the internally finned tube to be inspected in a range of ±10 mm. In the said figures, white lines in a grid shape are reflected images of the net made of steel wire used as the transparent plate that is provided in abutting relation relative to the end face of the internally finned tube.

As described above, the positions of the first annular light source 2A and the second annular light source 2B shown in FIGS. 1 and 2 described above are set based on distances $x_1$ and $x_2$ which are calculated according to the above described Formulae (1) and (2). When image acquisition by the camera is performed with each of the light sources 2A and 2B being placed at these positions, a real image shown in FIG. 5A is obtained. Moreover, when image acquisition is performed at a position where each of the light sources 2A and 2B is moved by 10 mm from this position in the direction to be back away from the internally finned tube, that is, at a position where the distance $x_1$ and the distance $x_2$ are added by 10 mm, a real image shown in FIG. 5B is obtained. On the other hand, when image acquisition is performed at a position where each of the light sources 2A and 2B is moved by 10 mm in the direction to be nearer to the internally finned tube, that is, at a position where the distance $x_1$ and the distance $x_2$ are subtracted by 10 mm, a real image shown in FIG. 5C is obtained. It is seen that real images shown in FIGS. 5A to 5C are equally clear. Thus, if the position of each of the light sources 2A and 2B is set within a range of ±10 mm along a tube axis direction from the position which is set based on the distance $x_1$ and the distance $x_2$ calculated according to Formula (1) and Formula (2) described above, it is possible to perform inspection at an equal accuracy.

A net made of steel wire can be used as the transparent plate 6 which constitutes the support member 5 shown in FIG. 1 described above and is provided in abutting relation relative to the tubular product 10. An example thereof is shown in FIG. 6 below.

Figure 6A:
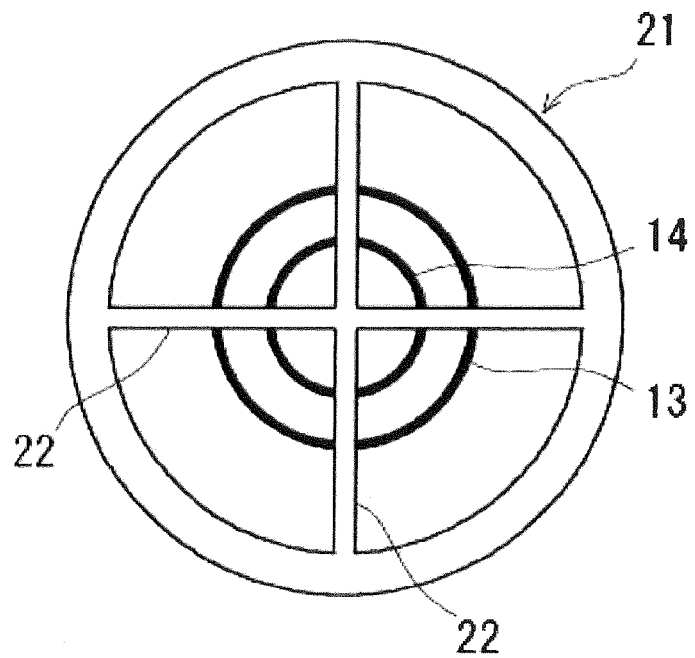
FIG. 6A shows a net made of steel wire having a cross-shaped mesh line.
Figure 6B:
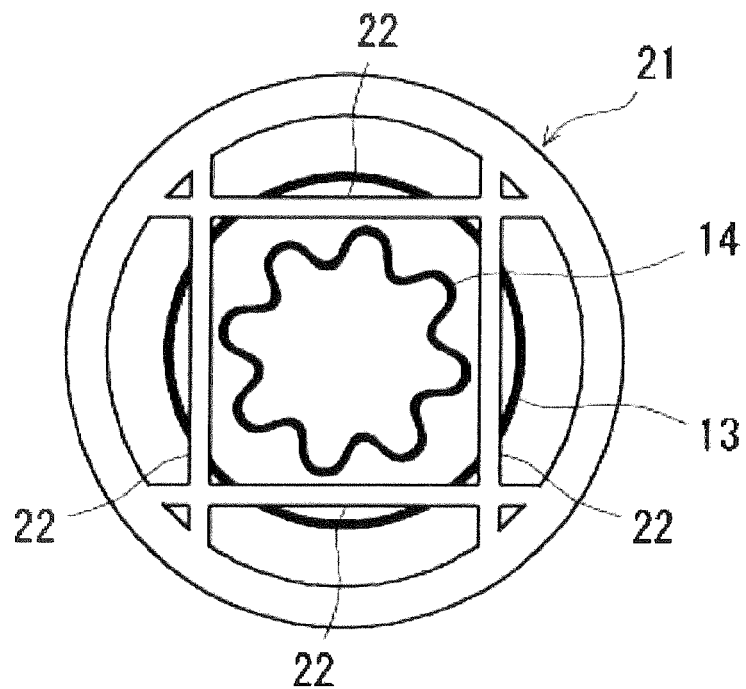
FIG. 6B shows a net made of steel wire having a grid-shaped mesh line.

FIG. 6 is a diagram showing an example of a net made of steel wire which constitutes a support member for supporting the camera and the light sources, and is provided in abutting relation relative to the tubular product, in which FIG. 6A shows a net made of steel wire having a cross-shaped mesh line, and FIG. 6B shows a net made of steel wire having a grid-shaped mesh line. It is noted that the said figures also show the external contour 13 and the internal contour 14 of the tubular product to be inspected. The net made of steel wire 21 shown in the figure can be fabricated by subjecting a metal disk of a thickness of about 2 mm to 3 mm to a stamping process. The width of the mesh line 22 of the net made of steel wire 21 is about 2 mm to 3 mm. The reason why the mesh line 22 is configured to have a thickness and a width of about 2 mm to 3 mm is that if it is too small, the rigidity becomes lower so that it will accidently deform when abutting the tubular product, and if it is too large, the mesh line is widely reflected into an image acquired by the camera, and the determination of the contour of the tubular product becomes difficult.

As shown in FIG. 6A, the net made of steel wire 21 having a cross-shaped mesh line 22 is suitable for the inspection of a normal tube of cross section composed of concentric circles as the tubular product. The positioning of the net made of steel wire 21 can be easily performed by aligning the center of the tubular product with the intersection of the mesh lines 22 as being the center of the net made of steel wire 21. Moreover, since there are only four intersections between the mesh line 22 and the external contour 13 and so are between it and the internal contour 14 of the tubular product, respectively, it is possible to determine the external contour 13 and the internal contour 14 without hindrance from an image acquired by the camera. This net made of steel wire 21 can also be used for the inspection of externally finned tubes.

As shown in FIG. 6B, the net made of steel wire 21 having a grid-shape mesh line 22 is suitable for the inspection of internally finned tubes as the tubular product. In this net made of steel wire 21, an opening between the mesh lines 22 is formed at the central portion such that the mesh line 22 intersects only with the external contour 13 of the internally finned tube. That is, the whole of the internal contour 14 of the internally finned tube is contained in the opening at the central portion. As a result of this, it is possible to determine the internal contour 14 without hindrance from an image acquired by the camera.

According to the inspection apparatus for a tubular product and the inspection method therefor, it is possible to perform the dimensional inspection for outer diameter and wall thickness at a high accuracy targeted for not only steel tubes having a simple shape, but also tubular products in which the shapes of the inner circumference or the outer circumference in the cross-section is not circular in a strict sense and include regular alterations, such as an internally finned tube, externally finned tube, etc. Furthermore, the inspection apparatus does not need any special mechanism for rotating the tubular product or the camera (including the light source) about the central axis of the tubular product, so that it is possible to realize the downsizing of the apparatus. In addition to those described above, according to the inspection apparatus for a tubular product and the inspection method therefor of the present invention, the inspection can be automated including the inner surface inspection of the tubular product.

INDUSTRIAL APPLICABILITY

The present invention can be effectively used in a dimensional inspection which is performed for quality assurance of tubular products, and further in an inner surface inspection.

REFERENCE SIGNS LIST

1: Camera, 2A: First annular light source, 2B: Second annular light source, 2C: Third annular light source, 5: Support member, 6: Transparent plate, 7: Annular plate, 8: Guide rod, 10: Tubular product, 11: End face, 12: Inner peripheral surface, 13: External contour, 14: Internal contour, 21: Net made of steel wire, 22: Mesh line, D: Outer diameter of tubular product, t: Wall thickness of tubular product

What is claimed is:

1. An apparatus for inspecting a tubular product, the apparatus comprising:
    a camera disposed on the central axis of the tubular product, the camera acquiring an image of the whole area of an end face of the tubular product;
    a first light source in which light as being inclined relative to the central axis of the tubular product is emitted from outside an image acquiring part of the camera, to illuminate only an outer peripheral edge of the end face side of the tubular product over the entire circumference thereof;
    a second light source interposed between the first light source and the camera, in which light as being inclined relative to the central axis of the tubular product is emitted from outside the image acquiring part of the camera to illuminate only an inner peripheral edge of the end face side of the tubular product over the entire circumference thereof, and
    a support member for supporting the first light source, the second light source, and the camera, the support member having a transparent plate that abuts the end face of the tubular product,
    wherein the inspection apparatus acquires an image of the tubular product with the camera while illuminating the tubular product with the first light source and the second light source, and calculates an outer diameter and a wall thickness of the tubular product based on the acquired image.

2. The inspection apparatus for a tubular product according to claim 1, wherein
    the first light source and the second light source are movable along the central axis direction of the tubular product.

3. The inspection apparatus for a tubular product according to claim 2, wherein the first light source and the second light source are configured with a large number of LEDs (light emitting diodes) being arranged in the form of a ring.

4. The inspection apparatus for a tubular product according to claim 3, wherein the transparent plate comprises a net made of steel wire.

5. The inspection apparatus for a tubular product according to claim 4, further comprising:
    a third light source interposed between the second light source and the camera, in which light as being inclined relative to the central axis of the tubular product is emitted from outside the image acquiring part of the camera to illuminate only an inner peripheral surface of the end face side of the tubular product over the entire circumference thereof,
    wherein the inspection apparatus acquires an image of the tubular product with the camera while illuminating the tubular product with the third light source, and detects surface defects on the inner peripheral surface of the tubular product based on the acquired image.

6. The inspection apparatus for a tubular product according to claim 3, further comprising:
    a third light source interposed between the second light source and the camera, in which light as being inclined relative to the central axis of the tubular product is emitted from outside the image acquiring part of the camera to illuminate only an inner peripheral surface of the end face side of the tubular product over the entire circumference thereof,
    wherein the inspection apparatus acquires an image of the tubular product with the camera while illuminating the tubular product with the third light source, and detects surface defects on the inner peripheral surface of the tubular product based on the acquired image.

7. The inspection apparatus for a tubular product according to claim 2, wherein the transparent plate comprises a net made of steel wire.

8. The inspection apparatus for a tubular product according to claim 7, further comprising:
    a third light source interposed between the second light source and the camera, in which light as being inclined relative to the central axis of the tubular product is emitted from outside the image acquiring part of the camera to illuminate only an inner peripheral surface of the end face side of the tubular product over the entire circumference thereof,
    wherein the inspection apparatus acquires an image of the tubular product with the camera while illuminating the tubular product with the third light source, and detects surface defects on the inner peripheral surface of the tubular product based on the acquired image.

9. The inspection apparatus for a tubular product according to claim 2, further comprising:
    a third light source interposed between the second light source and the camera, in which light as being inclined relative to the central axis of the tubular product is emitted from outside the image acquiring part of the camera to illuminate only an inner peripheral surface of the end face side of the tubular product over the entire circumference thereof, wherein the inspection apparatus acquires an image of the tubular product with the camera while illuminating the tubular product with the third light source, and detects surface defects on the inner peripheral surface of the tubular product based on the acquired image.

10. The inspection apparatus for a tubular product according to claim 1, wherein the first light source and the second light source are configured with a large number of LEDs (light emitting diodes) being arranged in the form of a ring.

11. The inspection apparatus for a tubular product according to claim 10, wherein the transparent plate comprises a net made of steel wire.

12. The inspection apparatus for a tubular product according to claim 11, further comprising:
 a third light source interposed between the second light source and the camera, in which light as being inclined relative to the central axis of the tubular product is emitted from outside the image acquiring part of the camera to illuminate only an inner peripheral surface of the end face side of the tubular product over the entire circumference thereof,
 wherein the inspection apparatus acquires an image of the tubular product with the camera while illuminating the tubular product with the third light source, and detects surface defects on the inner peripheral surface of the tubular product based on the acquired image.

13. The inspection apparatus for a tubular product according to claim 10, further comprising:
 a third light source interposed between the second light source and the camera, in which light as being inclined relative to the central axis of the tubular product is emitted from outside the image acquiring part of the camera to illuminate only an inner peripheral surface of the end face side of the tubular product over the entire circumference thereof,
 wherein the inspection apparatus acquires an image of the tubular product with the camera while illuminating the tubular product with the third light source, and detects surface defects on the inner peripheral surface of the tubular product based on the acquired image.

14. The inspection apparatus for a tubular product according to claim 1, wherein the transparent plate comprises a net made of steel wire.

15. The inspection apparatus for a tubular product according to claim 14, further comprising:
 a third light source interposed between the second light source and the camera, in which light as being inclined relative to the central axis of the tubular product is emitted from outside the image acquiring part of the camera to illuminate only an inner peripheral surface of the end face side of the tubular product over the entire circumference thereof,
 wherein the inspection apparatus acquires an image of the tubular product with the camera while illuminating the tubular product with the third light source, and detects surface defects on the inner peripheral surface of the tubular product based on the acquired image.

16. The inspection apparatus for a tubular product according to claim 1, further comprising:
 a third light source interposed between the second light source and the camera, in which light as being inclined relative to the central axis of the tubular product is emitted from outside the image acquiring part of the camera to illuminate only an inner peripheral surface of the end face side of the tubular product over the entire circumference thereof,
 wherein the inspection apparatus acquires an image of the tubular product with the camera while illuminating the tubular product with the third light source, and detects surface defects on the inner peripheral surface of the tubular product based on the acquired image.

\* \* \* \* \*